United States Patent
Spink et al.

(10) Patent No.: US 6,661,572 B2
(45) Date of Patent: Dec. 9, 2003

(54) ENHANCED SHUTTER CONTROL FOR IMAGE INSERTION IN A STEREO MICROSCOPE

(75) Inventors: Roger Spink, Berneck (CH); Jacques Alain Deverin, Widnau (CH); Benno Moser, Berneck (CH); Juergen Mannss, Oberdiessbach (CH)

(73) Assignee: Leica Microsystems AG, Heerbrugg (CH)

( * ) Notice: Subject to any disclaimer, the term of this patent is extended or adjusted under 35 U.S.C. 154(b) by 77 days.

(21) Appl. No.: 10/081,154

(22) Filed: Feb. 25, 2002

(65) Prior Publication Data

US 2002/0126375 A1 Sep. 12, 2002

(30) Foreign Application Priority Data

| Feb. 23, 2001 | (DE) | 101 08 988 |
| Feb. 23, 2001 | (DE) | 101 08 989 |
| Apr. 12, 2001 | (DE) | 101 18 702 |
| Apr. 12, 2001 | (DE) | 101 18 703 |
| Nov. 26, 2001 | (DE) | 101 57 613 |

(51) Int. Cl.$^7$ .............................................. G02B 21/18
(52) U.S. Cl. .................... 359/372; 359/377; 359/630
(58) Field of Search ............................. 359/368, 372, 359/373, 374, 375, 376, 377, 378, 381, 630, 638

(56) References Cited

U.S. PATENT DOCUMENTS 4,138,191 A    2/1979   Peyman et al.
6,473,229 B2 * 10/2002   Nakamura .................... 359/377

FOREIGN PATENT DOCUMENTS

WO         01/27659         4/2001

OTHER PUBLICATIONS

"Leica Dl C500: Dual Imaging Color Module." Leica Microsystems, Apr. 2002. Chicago, Illinois.
"Features and Benefits: The Ultra Observer, The Dual Imaging Module—Color and Monochrome." Leica Microsystems, Apr. 2001. Toronto, Canada.
"The Leica Imaging Module: Direct Integration of Images and Data into the Leica M500–N." Leica Microsystems, Oct. 1999.
"The Leica Dual Imaging and Ultra Observer: True Color Integration of Images and Data, Complete Assistants Observation." Leica Microsystems, Apr. 2001. Toronto, Canada.

* cited by examiner

*Primary Examiner*—Mark A. Robinson
(74) *Attorney, Agent, or Firm*—Foley & Lardner (57) ABSTRACT

A stereo microscope comprises: a main objective; a main observation output configured so that a left-hand beam path and a right-hand beam path are formed between the main objective and the main observation output; at least one input reflection beam splitter in each of the left-hand and right-hand beam paths configured to reflect additional information into its corresponding beam path; at least one output reflection beam splitter in at least one of the left-hand and right-hand beam paths; at least one first switchable shutter associated with at least one of the left-hand and right-hand beam paths, located in front of a corresponding input reflection beam splitter; and at least one second switchable shutter associated with at least one of the left-hand and right-hand beam paths, located between the main observation output and a corresponding output reflection beam splitter.

23 Claims, 4 Drawing Sheets

ENHANCED SHUTTER CONTROL FOR IMAGE INSERTION IN A STEREO MICROSCOPE

CROSS-REFERENCE TO RELATED PATENT APPLICATIONS

This invention claims priority to German Priority Application 101 08 988.0, filed Feb. 23, 2001, which is incorporated herein by reference in its entirety. This invention claims priority to German Priority Application 101 08 989.9, filed Feb. 23, 2001, which is incorporated herein by reference in its entirety. This invention claims priority to German Priority Application 101 18 702.5, filed Apr. 12, 2001, which is incorporated herein by reference in its entirety. This invention claims priority to German Priority Application 101 18 703.3, filed Apr. 12, 2001, which is incorporated herein by reference in its entirety. This invention claims priority to German Priority Application 101 57 613.7, filed Nov. 26, 2001, which is incorporated herein by reference in its entirety.

1. Field of the Invention

The invention relates to shutter control for the integration of additional data into an observation beam path or a plurality of observation beam paths of a stereo microscope, for selectively switching off an undesired observation channel.

2. Background of the Invention

In modern surgical microscopes, it is customary to insert additional information into one of the two intermediate images. This additional information is either superimposed directly on the optical object image (e.g., correlated data, CT, MRI, contours) or displayed without reference to the optical object image (non-correlated image data, standard sections, etc.), by stopping the relevant object beam or superimposing it in a limited subregion (monitoring curves, menus, etc.).

In the case of stopping the object beam, a shutter is moved into the object beam path between the object and the beam splitter which inserts the additional information, so that only the additionally inserted information can be seen. This known shutter arrangement was publicized in written form in WO-A2-01/27659 dated Apr. 19, 2001 (after the priority date of the present application), but had previously been demonstrated by Leica under the designation "BIV" as a module for surgical microscopes. However, neither the "BIV" nor WO-A2-01/27659 offers the option of being able to permit a number of users to observe the additional information and/or the object image as desired by utilizing the further course of the beam. Instead, the figures of WO-A2-01/27659 make it clear that a possible first assistant at the assistant port (11) can see only the object image, but not the additional information reflected in from the display (1). A second assistant who, for example, takes a view via an eyepiece on the second assistant tube 19, now sees only one image channel (the right-hand main beam path (18)) and can thus optionally see either the object image or nothing (if the third shutter 20 is closed), but in each case this is not independent of the main observer at the eyepiece (15) who always sees, in the right-hand main beam path (18), the same image as the second assistant. In this arrangement, the latter problem could be solved only by an additional reflecting device provided for the third main beam path (see page 4, line 14 to page 5, line 19 of WO-A2-01/27659). The disclosure of WO-A2-01/27659 is hereby incorporated by reference.

For the reason specified, the known systems lack flexibility for the control of the observation facilities. In addition, in the known systems, a restriction is imposed to the extent that the reflection into both main beam paths (4 and 13)—as already mentioned—requires two reflecting devices (1, 2, 3 and so on), which requires additional space and an increased microscope size.

Zeiss, Oberkochen, Germany, makes a "Multivision" construction, which permits an assistant to see the same image as a main observer, irrespective of whether this is an object image alone or an object image with an additional image superimposed on it. The flexibility in the observation facility is therefore disadvantageously likewise restrictive.

Figure 5:
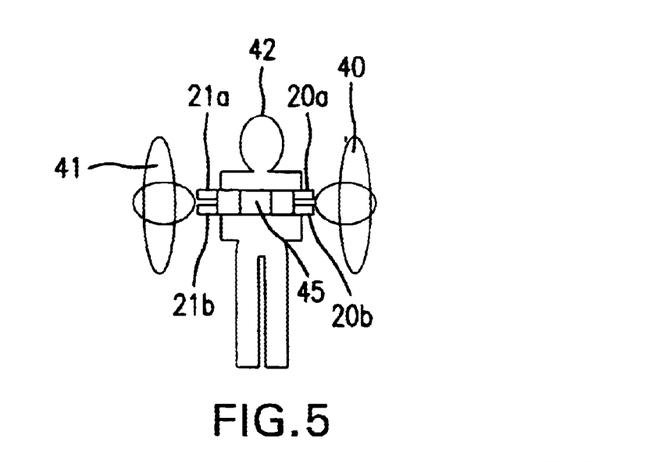
FIGS. 5–7 illustrate the known positioning variants of the surgeon and the assistant with respect to the patient being observed.
Figure 6:
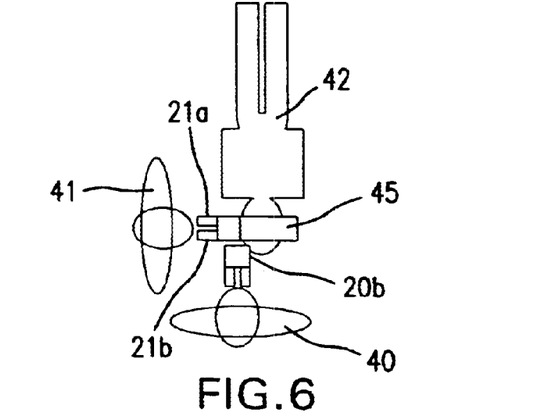
Figure 7:
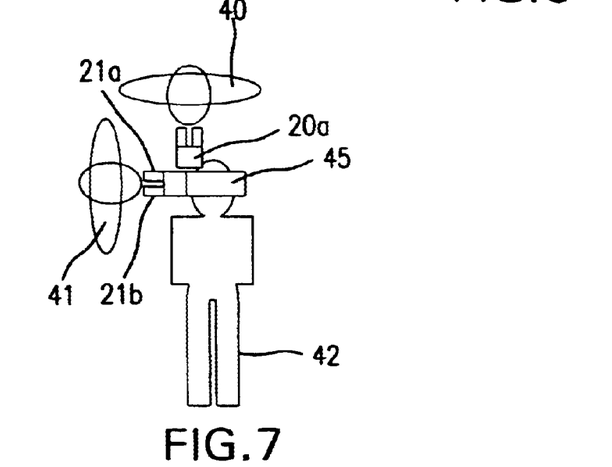

In surgical microscopes, a distinction is to be drawn in principle with regard to their functions between three different types of observation or application. Reference is made to FIGS. 5–7 which show examples of microscope settings. The following reference numerals and designations appear in the Figures: Patient or object 42, lens holder (of a surgical microscope) 45, surgeon (main observer) 41, assistant 40, observation output (main eyepiece) having observation outputs 21*a* and 21*b* corresponding to a left-hand beam path and right-hand beam path, respectively, observation output (assistant eyepiece) having observation outputs 20*a* and 20*b* for stereoscopic observation (as in FIG. 5) or, for monocular observation, observation output 20*b* corresponding to the right-hand beam path (as in FIG. 6) and observation output 20*a* corresponding to the left-hand beam path (as in FIG. 7).

There are at least three kinds of observers of the information provided by a microscope: a surgeon 41, an assistant 40, and an observer group.

A surgeon 41, who in principle (almost exclusively) uses the observation outputs 21*a* and 21*b* stereoscopically, generally decides as to the type and time of the input reflection of the additional information, and as to whether or not to superimpose the additional information.

An assistant 40 almost exclusively uses either the right-hand observation output 20*b* (as in FIG. 6) or the left-hand observation beam path 20*a* (as in FIG. 7) monoscopically, when he/she is standing at right angles to the surgeon 41 and the microscope (such as in craniotomy). Alternatively, the assistant 40 uses the observation beam path 20*a* and 20*b* stereoscopically when the assistant 40 stands opposite the surgeon 41 and behind the microscope, as illustrated in FIG. 5 (such as in spinal operations).

An observer group, that is beside the microscope or even outside the operating room, is intended to see substantially that information (on a monitor in or outside the operating room) which the surgeon 41 sees. Thus, members of the observer group do not themselves look through the microscope at all, but carry out the observation via a video recording.

Owing to the additional information in a single image channel, in particular in the case of data substitution by the insertion of video data, for example, into this image channel (as compared with the second image channel), the surgeon 41 is provided with two different items of information, which may irritate him/her, when looking stereoscopically into the two eyepieces.

SUMMARY OF THE INVENTION

It is therefore a central object of the present invention to eliminate the aforementioned disadvantages and to increase the flexibility of the observation facilities and, preferably, also to achieve this as far as possible without additional input reflection devices (i.e., without additional beam paths and measures which enlarge the subassembly).

The present invention provides for the use of additional shutters and a novel shutter control, which permits the surgeon to switch off the object images if so desired and to manage the image information made available to the respective (main and/or assistant) observers.

The desired flexibility in the observation facility is achieved in that, in at least one beam path, at least a second switchable shutter is arranged between the output reflection beam splitter and the main observation output, and in that an input reflection beam splitter is arranged in each main beam path. In this way, image information can be provided flexibly to a plurality of assistants and the main observer as desired, to some extent irrespective of that which is supplied to the main observer.

This flexibility is optimized when, between each input reflection beam splitter and the main objective, and each output reflection beam splitter and the main observation output, a switchable first and second shutter is arranged, respectively. A switchable shutter according to the present invention is understood to be any shutter device which opens or closes a beam path. This therefore comprises both mechanical and optoelectronic shutters or the like.

A further increase in the flexibility in the observation facility, an improvement in the applicability, and also a reduction of unnecessary light losses or the like, can be achieved in a stereo microscope according to the present invention having at least one secondary observation output (e.g., assistant output) if, between at least one output reflection beam splitter and the secondary observation output, a third switchable shutter is also arranged. In a preferred aspect, a third switchable shutter is arranged for each secondary observation output.

Further, in the case of stereo microscopes in which, for each main beam path, at least two secondary observation outputs are provided, it is advantageous if these observation outputs lie in the same radial plane in relation to the main beam path. For example, the present invention provides for one output located to the side of the output reflection beam path and one output located behind the output reflection beam splitter (so that the outputs may be offset by, for example, approximately 90°), where the output reflection beam splitter is rotatable, so that it supplies the output reflection image information optionally to one or the other secondary observation output.

Because the above aspect of the present invention may cause image rotation, this may be taken into account and corrected electronically (in a video signal) according to the invention. More information on this feature may be gathered from DE-A-10108989 (application date of Feb. 23, 2001), the disclosure of which is hereby incorporated by reference.

A particularly small overall size results in the case of a stereo microscope according to the present invention in which at least one of the input reflection beam splitters is at the same time also designed as an output reflection beam splitter, for example for video image sensors or else other image recording devices.

In another preferred aspect of the present invention, space-saving results if both input reflection beam splitters in the two main beam paths are assigned a common input reflection beam path, which can optionally be connected to one or the other or both input reflection beam splitters. More information on this feature may be gathered from DE-A-10108988 (application date Feb. 23, 2001), the disclosure of which is hereby incorporated by reference. In one aspect, the input reflection beam path comprises a deflection prism, which can preferably be rotated or pivoted to be optionally assigned to the left-hand or right-hand main beam path. In another aspect, as specified in the second figure of DE-A-10108988, the deflection prism is not arranged between the input reflection beam splitters but behind them, which advantageously does not cause any image rotation.

According to a further aspect of the present invention, at least some of the shutters are connected to a control device which, in the operating state, closes or opens at least some of the shutters on the basis of application- and/or user-specific points of view. Thus, for example, a user can define his or her personal application profile and call this up again at any time as required, without having to perform complicated presettings again.

The control tasks are made easier if at least one setting or position detector is provided which, in the operating state, detects the setting or position of the output reflection prisms and/or the deflection prism and/or the shutters, is connected to the control device, and aligns the shutters appropriately. In this way, even manual override settings can be taken into account and erroneous switching actions can be avoided.

In a further aspect, the control device may be connected to a controller (e.g., video controller) for the additional information reflected in, in order, as a function of the respective setting of the output reflection prisms and/or the deflection prism and/or the respective shutter setting and/or the respective observer wishes, to influence the image reflected in via a display, so that the respective user is automatically provided with the desired or requisite image information.

The control device may comprise, for example, at least one shutter controller, at least one controller with memory for data-type information and user setup and/or at least one controller having sensors to sense the position of the output reflection beam splitters and/or the deflection prism. The latter may be set automatically and/or manually.

The efficiency of IGS (image guided surgery) operations may be increased if the control device is connected to the operation control device (IGS) and, in the operating state, signals at least the insertion state to the left-hand or right-hand main beam path.

The present invention provides for a stereo microscope, comprising: a main objective; a main observation output configured so that a left-hand beam path and a right-hand beam path are formed between the main objective and the main observation output; at least one input reflection beam splitter in each of the left-hand and right-hand beam paths configured to reflect additional information into its corresponding beam path; at least one output reflection beam splitter in at least one of the left-hand and right-hand beam paths; at least one first switchable shutter associated with at least one of the left-hand and right-hand beam paths, located in front of a corresponding input reflection beam splitter with respect to a path direction of the corresponding beam path, configured to be able to prevent object information from passing therethrough; and at least one second switchable shutter associated with at least one of the left-hand and right-hand beam paths, located between the main observation output and a corresponding output reflection beam splitter. The stereo microscope may be a surgical microscope.

In one aspect of the present invention, the stereomicroscope may comprise exactly two input reflection beam splitters and exactly two first switchable shutters, wherein one input reflection beam splitter is in each of the left-hand and right-hand beam paths. Further, the stereomicroscope may comprise exactly two output reflection beam splitters and exactly two second switchable shutters, wherein one output reflection beam splitter is in each of the left-hand and right-hand beam paths.

In another aspect of the present invention, the stereomicroscope may comprise a secondary observation output associated with a corresponding output reflection beam splitter, wherein the corresponding output reflection beam splitter is configured to reflect out a portion of a beam toward the secondary observation output. The stereomicroscope may further comprise a third switchable shutter located between the corresponding output reflection beam splitter and the secondary observation output.

In another aspect of the present invention, the stereomicroscope may comprise exactly two output reflection beam splitters, exactly two secondary observation outputs, and exactly two third switchable shutters, wherein one third switchable shutter is located between one output reflection beam splitter and one secondary observation output, and the other third switchable shutter is located between the other output reflection beam splitter and the other secondary observation output.

In another aspect of the present invention, the stereomicroscope may comprise exactly one output reflection beam splitter and a group of at least two secondary observation outputs associated with the output reflection beam splitter, wherein the output reflection beam splitter is rotatable about an axis substantially parallel to its corresponding beam path, wherein the secondary observation outputs in the group are located in the same plane that is perpendicular to their corresponding beam path, and wherein the output reflection beam splitter is configured to reflect out a portion of a beam toward one secondary observation output when the output reflection beam splitter is in one rotational position and toward another secondary observation output when the output reflection beam splitter is in another rotational position.

In another aspect of the present invention, the stereomicroscope may comprise exactly one output reflection beam splitter for each of the left-hand and right-hand beam paths, and a group of at least two secondary observation outputs associated with each output reflection beam splitter, wherein each output reflection beam splitter is rotatable about an axis substantially parallel to its corresponding beam path, wherein the secondary observation outputs in each group are located in the same plane that is substantially perpendicular to their corresponding beam path, and wherein each output reflection beam splitter is configured to reflect out a portion of a beam toward one secondary observation output when the output reflection beam splitter is in one rotational position and toward another secondary observation output when the output reflection beam splitter is in another rotational position.

In another aspect of the present invention, at least one input reflection beam splitter may also be configured as an output reflection beam splitter.

In another aspect of the present invention, the input reflection beam splitters may have a common input reflection beam path, wherein additional information may be reflected from the common input reflection beam path into one of the left-hand and right-hand beam paths.

In another aspect of the present invention, the stereomicroscope may comprise a deflection prism configured to reflect additional information from the common input reflection beam path toward one of the input reflection beam splitters. The deflection prism may be movable from a position in which it is configured to reflect additional information from the common input reflection beam path toward one of the input reflection beam splitters to another position in which it is configured to reflect additional information from the common input reflection beam path toward another of the input reflection beam splitters.

In another aspect of the present invention, the stereomicroscope may comprise a control device configured to open and close at least one of the switchable shutters. The control device may be configured to open and close at least one of the switchable shutters based on a manual operator instruction. Alternatively, the control device may comprise a memory configured to store operator-specific or application-specific instructions, wherein the control device may be configured to automatically open and close at least one of the switchable shutters on the basis of the instructions.

In another aspect of the present invention, at least one output reflection beam splitter may be rotatable about an axis substantially parallel to its corresponding beam path, wherein the stereomicroscope further comprises: a movable deflection prism configured to reflect additional information from a common input reflection beam path toward one of the input reflection beam splitters; a position detector configured to detect a position of at least one of the rotatable output reflection beam splitters, the switchable shutters, and the movable deflection prism; and a control device connected to the position detector and configured to open and close at least one of the switchable shutters as a function of one of the position detected by the position detector and operator instructions. The control device may be configured to control the additional information as a function of one of the position detected by the position detector and operator instructions.

In another aspect of the present invention, the inventive control for the shutters of the novel stereomicroscope may be combined with a control of a stereo tactical operation system for guiding a surgeon when doing the operation. The combination providing that the one control influences the other control for optimal switching and disclosing in which ray beam the inserted images are displayed.

BRIEF DESCRIPTION OF THE DRAWINGS

FIG. 3 shows a schematic view of a microscope according to a preferred embodiment of the present invention, with one first switchable shutter 17b open, one first switchable shutter 17a closed, and both second switchable shutters 18a, 18b open, and where the additional information is reflected into the left-hand beam path 2a.

FIG. 4 shows a schematic view of a microscope according to a preferred embodiment of the present invention, with one first switchable shutter 17b open, one first switchable shutter 17a closed, both second switchable shutters 18a, 18b open, and both third switchable shutters 19a, 19b open, and where the additional information is reflected into the left-hand beam path 2a.

DETAILED DESCRIPTION OF THE PREFERRED EMBODIMENTS

Figure 1:
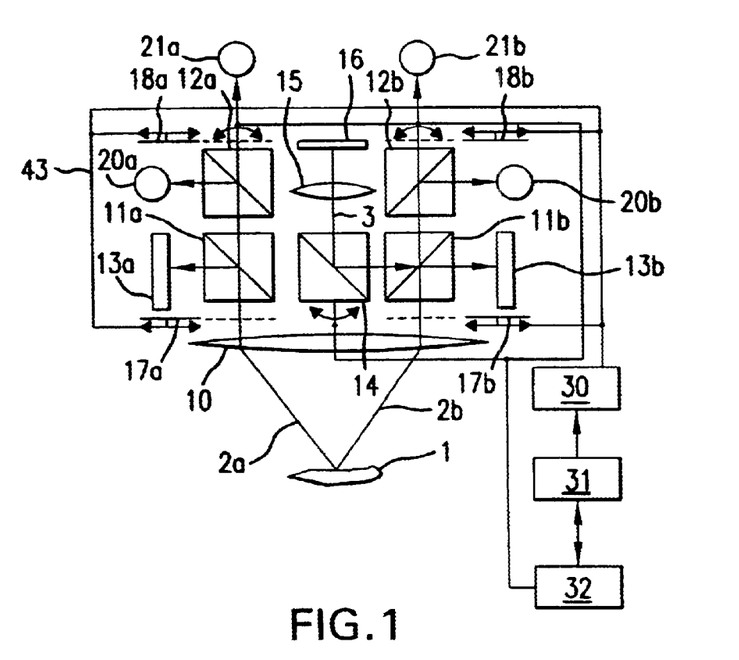
FIG. 1 shows a schematic view of a microscope according to a preferred embodiment of the present invention, with both first switchable shutters 17a, 17b open and both second switchable shutters 18a, 18b open, and where the additional information is reflected into the right-hand beam path 2b.

In FIG. 1, a display 16 projects an image provided with additional information along the common input reflection beam path 3 for the additional information and into the right-hand beam path 2b by means of a lens 15 and a switchable or movable deflection prism 14 (which may be switched for projection into the left-hand beam path 2a or the right-hand beam path 2b). By means of the input reflection beam splitter 11b, this additional information may be superimposed on the image of the object 1 (and may be further supplied to the optional image sensor 13b and other observation beam paths). Left-hand and right-hand beam paths 2a, 2b are created in part by a main objective 10.

In FIGS. 1–4, a control line 43 connects the shutter controller 30, the controller 31 having memory, and the position detector 32 with the first switchable shutters 17a, 17b, the second switchable shutters 18a, 18b, the deflection prism 14, and the (optionally rotatable) output reflection beam splitters 12a, 12b, so that the shutters and prisms/splitters may be controlled and/or their positions/settings detected. At the points at which position detection is possible, a point is drawn on the control line 43. Shutters in the stereoscopic beam paths can also be coupled to one another mechanically.

Figure 2:
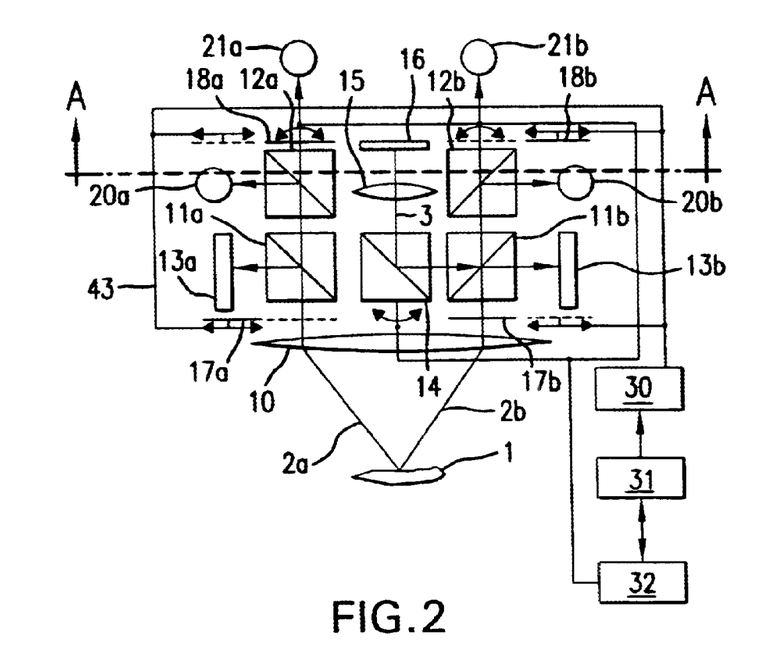
FIG. 2 shows a schematic view of a microscope according to a preferred embodiment of the present invention, with one first switchable shutter 17a open, one first switchable shutter 17b closed, one second switchable shutter 18b open, and one second switchable shutter 18a closed, and where the additional information is reflected into the right-hand beam path 2b.

By means of the shutters 18a and 18b, the observer, if desired, can concentrate on just the additional information. FIG. 1 shows all shutters 17a, 17b, 18a, 18b open. In FIG. 2, like in FIG. 1, the additional information is switched to the right-hand beam path 2b. However, in FIG. 2, shutters 18a and 17b are closed, thus allowing the surgeon 41 to view only the right-hand beam path 2b via the right-hand observation output 21b. Because shutter 17b is closed, the surgeon 41 sees only the additional information with the right eye. Because shutter 18a is closed, the left eye does not see anything.

The assistant observation outputs 20a, 20b may likewise be switched either to the two lateral monoscopic outputs (as in FIGS. 6 and 7) or to the rear stereoscopic output (as in FIG. 5), depending on the surgical intervention.

In a cranial intervention, utilizing the configuration shown in FIG. 2, an assistant 40 positioned on the left-hand side sees the object information monoscopically through the left-hand observation output 20a, but does not see the additional information; an assistant 40 positioned on the right-hand side perceives only the additional information monoscopically through the right-hand observation output 20b, like the surgeon 41.

Figure 3:
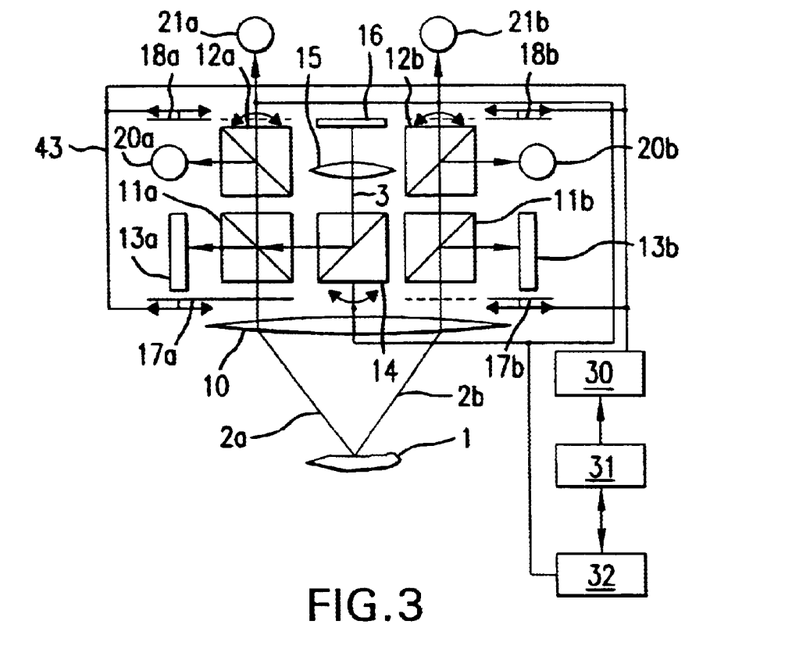

FIG. 3 shows the setting with inserted additional information in the left-hand beam path 2a with shutters 17b, 18a, 18b open and shutter 17a closed.

In a spinal intervention, utilizing the configuration shown in FIG. 3, the assistant 40 perceives both items of information stereoscopically through the outputs 20a and 20b. He/she therefore also sees both items of information with differing content.

Particular surgeons' preferences can be stored in the controller 31 and called up for use. For example, surgeon A always likes to see both items of information at the same time (in which case the shutters 18a and 18b always remain open), while surgeon B only likes to see the additional information (in which case, depending on the position of the prism 14, the shutter controller 30 closes shutter 18a or 18b).

Figure 4:
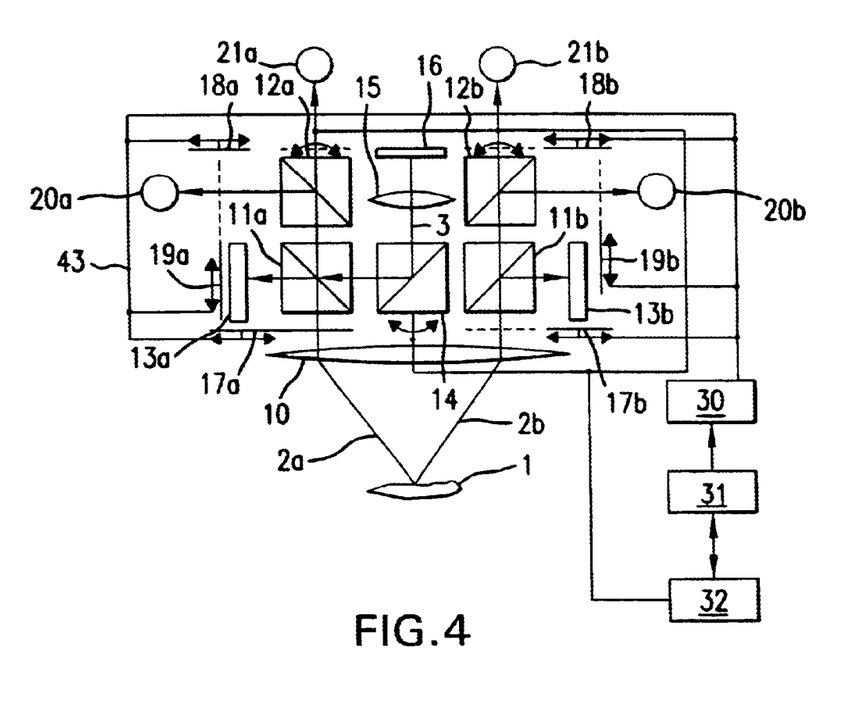

FIG. 4 illustrates the arrangement of the shutters for the assistant observation outputs 20a, 20b. These are essentially the shutters 19a and 19b, one of which may be closed if an assistant 40 is positioned behind (such as in a spinal arrangement) and the assistant 40 prefers to see the information in only one beam path.

The invention provides at least the following advantages: selectively switching off an object image which is temporarily undesired or which distracts the surgeon 41; providing the assistant 40 with an image of the object 1 in any application; enabling a connected camera system (such as an image sensor 13a, 13b) to always detect the object 1; and automatically adapting the shutter positions depending on the additional information, pre-programmed instructions, or operator preferences.

Also, in FIGS. 1–4, input reflection beam splitters 11a, 11b may also serve as output reflection beam splitters. For example, as shown in FIG. 1, the additional information is reflected out of the common input reflection beam path 3 by the deflecting prism 14 and into the right-hand beam path 2b by the input reflection beam splitter 11b. Further, part of the light emitted from the object 1 and passing through the main objective 10 (i.e., the object image) is reflected out of the right-hand beam path 2b toward the image sensor 13b by the input reflection beam splitter 11b. Here, the input reflection beam splitter 11b is also serving as an output reflection beam splitter.

Figure 8:
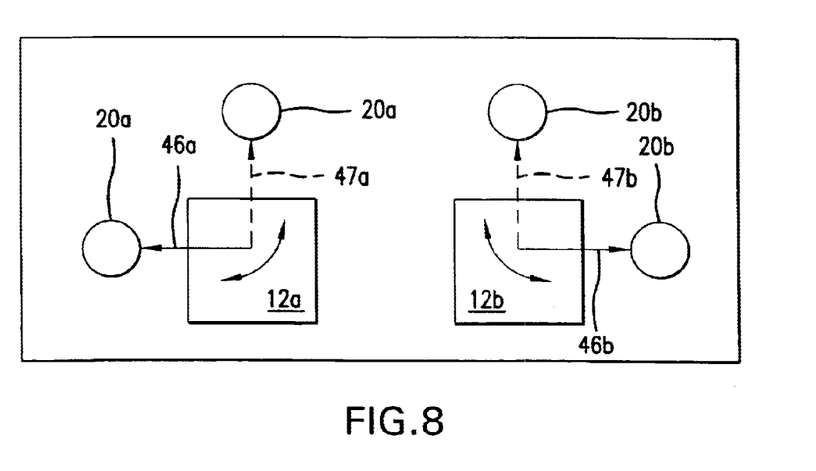
FIG. 8 shows a cross section along section A—A as shown in FIG. 2.

FIG. 8 shows a cross section of the microscope shown in FIG. 2 along a cross-sectional plane designated by A—A. FIG. 8 demonstrates another possible feature of the present invention, where the output reflection beam splitters 12a, 12b are movable or rotatable about an axis that is substantially parallel to its corresponding beam path. In other words, output reflection beam splitter 12a may be rotatable about an axis that is substantially parallel to the left-hand beam path 2a, and similarly for the output reflection beam splitter 12b. Thus, the output of each output reflection beam splitter 12a, 12b is always approximately parallel to a plane of the cross section A—A (i.e., the plane of the page on which FIG. 8 is drawn, which is approximately perpendicular to each of the left-hand and right-hand beam paths 2a, 2b). FIG. 8 shows an embodiment in which each output reflection beam splitter 12a, 12b has a group of two observation outputs 20a, 20b associated with it, and the observation outputs 20a, 20b are located in the plane of the cross section A—A (i.e., the plane of the page on which FIG. 8 is drawn). The solid arrows 46a, 46b designate one possible rotational position of the output reflection beam splitters 12a, 12b, and the dashed lines 47a, 47b designate another possible rotational position of the output reflection beam splitters 12a, 12b. In FIG. 8, the observation outputs 20a are separated by approximately 90°, although any other angle could be used. There could, of course, be more observations outputs 20a, 20b for the output reflection beam splitters 12a, 12b.

The foregoing description of a preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described to explain the principles of the invention and as a practical application to enable one skilled in the art to utilize the invention in various embodiments and with various modifications suited to the particular use contemplated. It is intended that the scope of the invention be defined by the claims appended hereto and their equivalents.

List of Designations

1 Object (patient)
2a Main beam path=object beam, left-hand beam path
2a Main beam path=object beam, right-hand beam path
3 Input reflection beam path for additional information
10 Main objective
11a Input reflection beam splitter for left-hand beam path, video and additional information
11b Input reflection beam splitter for right-hand beam path, video and additional information
12a Output reflection beam splitter for left-hand beam path, first and second observer
12b Output reflection beam splitter for right-hand abeam path, first and second observer
13a Video image sensor for left-hand beam path
13a Video image sensor for right-hand beam path
14 (Switchable) deflection prism (additional information beam path
15 Imaging objects for (16)
16 Display for additional information
17a Switchable first shutter for stooping the object light in the left-hand beam path
17b Switchable first shutter for stooping the object light in the right-hand beam path
18a Switchable second shutter for stooping the object light in the left-hand beam path
18b Switchable second shutter for stooping the object light in the right-hand beam path
19a Switchable third shutter for stooping the object light in the left-hand beam path
19b Switchable third shutter for stooping the object light in the right-hand beam path
20a Secondary observation output (assistant output) for monocular observer (40), left
20b Secondary observation output (assistant output) for monocular observer (40), right
21a Main observation output for stereo observation for (41), left-hand beam path
21b Main observation output for stereo observation for (41), right-hand beam path
30 Shutter controller (for detecting the position or setting and/or for controlling the shutters)
31 Controller for data-type information with memory and user setup
32 Control and sensors of the rotation prisms (for detecting the position or setting and/or for controlling the prisms
40 Assistant
41 Surgeon
42 Patient
45 Lens holder

What is claimed is:
1. A stereo microscope comprising:
a main objective;
a main observation output configured so that a left-hand beam path and a right-hand beam path are formed between the main objective and the main observation output;
at least one input reflection beam splitter in each of the left-hand and right-hand beam paths configured to reflect additional information into its corresponding beam path;
at least one output reflection beam splitter in at least one of the left-hand and right-hand beam paths;
at least one first switchable shutter associated with at least one of the left-hand and right-hand beam paths, located in front of a corresponding input reflection beam splitter with respect to a path direction of the corresponding beam path, configured to be able to prevent object information from passing therethrough; and
at least one second switchable shutter associated with at least one of the left-hand and right-hand beam paths, located between the main observation output and a corresponding output reflection beam splitter.

2. A stereomicroscope as in claim 1, wherein the stereo microscope is a surgical microscope.

3. A stereomicroscope as in claim 1, comprising exactly two input reflection beam splitters and exactly two first switchable shutters, wherein one input reflection beam splitter is in each of the left-hand and right-hand beam paths.

4. A stereomicroscope as in claim 1, comprising exactly two output reflection beam splitters and exactly two second switchable shutters, wherein one output reflection beam splitter is in each of the left-hand and right-hand beam paths.

5. A stereomicroscope as in claim 1, further comprising a secondary observation output associated with a corresponding output reflection beam splitter, wherein the corresponding output reflection beam splitter is configured to reflect out a portion of a beam toward the secondary observation output.

6. A stereomicroscope as in claim 5, further comprising a third switchable shutter located between the corresponding output reflection beam splitter and the secondary observation output.

7. A stereomicroscope as in claim 6, comprising exactly two output reflection beam splitters, exactly two secondary observation outputs, and exactly two third switchable shutters, wherein one third switchable shutter is located between one output reflection beam splitter and one secondary observation output, and the other third switchable shutter is located between the other output reflection beam splitter and the other secondary observation output.

8. A stereomicroscope as in claim 1, comprising exactly one output reflection beam splitter and a group of at least two secondary observation outputs associated with the output reflection beam splitter, wherein the output reflection beam splitter is rotatable about an axis substantially parallel to its corresponding beam path, wherein the secondary observation outputs in the group are located in the same plane that is perpendicular to their corresponding beam path, and wherein the output reflection beam splitter is configured to reflect out a portion of a beam toward one secondary observation output when the output reflection beam splitter is in one rotational position and toward another secondary observation output when the output reflection beam splitter is in another rotational position.

9. A stereomicroscope as in claim 1, comprising exactly one output reflection beam splitter for each of the left-hand and right-hand beam paths, and a group of at least two secondary observation outputs associated with each output reflection beam splitter, wherein each output reflection beam splitter is rotatable about an axis substantially parallel to its corresponding beam path, wherein the secondary observation outputs in each group are located in the same plane that is substantially perpendicular to their corresponding beam path, and wherein each output reflection beam splitter is configured to reflect out a portion of a beam toward one secondary observation output when the output reflection beam splitter is in one rotational position and toward another secondary observation output when the output reflection beam splitter is in another rotational position.

10. A stereomicroscope as in claim 1, wherein at least one input reflection beam splitter is also configured as an output reflection beam splitter.

11. A stereomicroscope as in claim 1, wherein the input reflection beam splitters have a common input reflection beam path, wherein additional information may be reflected from the common input reflection beam path into one of the left-hand and right-hand beam paths.

12. A stereomicroscope as in claim 11, further comprising a deflection prism configured to reflect additional information from the common input reflection beam path toward one of the input reflection beam splitters.

13. A stereomicroscope as in claim 12, wherein the deflection prism is movable from a position in which it is configured to reflect additional information from the common input reflection beam path toward one of the input reflection beam splitters to another position in which it is configured to reflect additional information from the common input reflection beam path toward another of the input reflection beam splitters.

14. A stereomicroscope as in claim 1, further comprising a control device configured to open and close at least one of the switchable shutters.

15. A stereomicroscope as in claim 14, wherein the control device is configured to open and close at least one of the switchable shutters based on a manual operator instruction.

16. The stereomicroscope as in claim 15, in combination with a stereotactic surgical construction and an image-controlled operation control device, wherein the control device is connected to the operation control device and, in the operating state, signals at least an insertion state into the left-hand or right-hand beam path.

17. A stereomicroscope as in claim 14, wherein the control device comprises a memory configured to store operator-specific or application-specific instructions, wherein the control device is configured to automatically open and close at least one of the switchable shutters on the basis of the instructions.

18. The stereomicroscope as in claim 17, in combination with a stereotactic surgical construction and an image-controlled operation control device, wherein the control device is connected to the operation control device and, in the operating state, signals at least an insertion state into the left-hand or right-hand beam path.

19. The stereomicroscope as in claim 14, in combination with a stereotactic surgical construction and an image-controlled operation control device, wherein the control device is connected to the operation control device and, in the operating state, signals at least an insertion state into the left-hand or right-hand beam path.

20. A stereomicroscope as in claim 1, wherein at least one output reflection beam splitter is rotatable about an axis substantially parallel to its corresponding beam path, wherein the stereomicroscope further comprises: a movable deflection prism configured to reflect additional information from a common input reflection beam path toward one of the input reflection beam splitters; a position detector configured to detect a position of at least one of the rotatable output reflection beam splitters, the switchable shutters, and the movable deflection prism; and a control device connected to the position detector and configured to open and close at least one of the switchable shutters as a function of one of the position detected by the position detector and operator instructions.

21. A stereomicroscope as in claim 20, wherein the control device is configured to control the additional information as a function of one of the position detected by the position detector and operator instructions.

22. The stereomicroscope as in claim 21, in combination with a stereotactic surgical construction and an image-controlled operation control device, wherein the control device is connected to the operation control device and, in the operating state, signals at least an insertion state into the left-hand or right-hand beam path.

23. The stereomicroscope as in claim 20, in combination with a stereotactic surgical construction and an image-controlled operation control device, wherein the control device is connected to the operation control device and, in the operating state, signals at least an insertion state into the left-hand or right-hand beam path.

* * * * *